(12) United States Patent
Ronen

(10) Patent No.: US 11,833,115 B2
(45) Date of Patent: Dec. 5, 2023

(54) MINERAL BASED COMPOSITIONS AND USE THEREOF

(71) Applicant: ANJON BIOLOGICS, INC., Las Vegas, NV (US)

(72) Inventor: Raziel Ronen, Hod Hasharon (IL)

(73) Assignee: ANJON BIOLOGICS, INC., Las Vegas, NV (US)

( * ) Notice: Subject to any disclaimer, the term of this patent is extended or adjusted under 35 U.S.C. 154(b) by 211 days.

(21) Appl. No.: 17/086,859

(22) Filed: Nov. 2, 2020

(65) Prior Publication Data

US 2021/0251880 A1   Aug. 19, 2021

Related U.S. Application Data

(63) Continuation of application No. 15/511,579, filed as application No. PCT/IB2015/057264 on Sep. 21, 2015, now abandoned.

(60) Provisional application No. 62/054,040, filed on Sep. 23, 2014.

(51) Int. Cl.
| | | |
|---|---|---|
| *A61K 8/97* | (2017.01) |
| *A61K 33/04* | (2006.01) |
| *A61K 33/30* | (2006.01) |
| *A61K 31/4166* | (2006.01) |
| *A61K 8/19* | (2006.01) |
| *A61K 8/23* | (2006.01) |
| *A61K 8/25* | (2006.01) |
| *A61K 8/27* | (2006.01) |
| *A61K 8/36* | (2006.01) |
| *A61K 8/49* | (2006.01) |
| *A61K 8/67* | (2006.01) |
| *A61K 8/92* | (2006.01) |
| *A61K 8/96* | (2006.01) |
| *A61Q 17/04* | (2006.01) |

(52) U.S. Cl.
CPC .................. *A61K 8/97* (2013.01); *A61K 8/19* (2013.01); *A61K 8/23* (2013.01); *A61K 8/25* (2013.01); *A61K 8/27* (2013.01); *A61K 8/36* (2013.01); *A61K 8/4946* (2013.01); *A61K 8/671* (2013.01); *A61K 8/678* (2013.01); *A61K 8/922* (2013.01); *A61K 8/965* (2013.01); *A61K 31/4166* (2013.01); *A61K 33/04* (2013.01); *A61K 33/30* (2013.01); *A61Q 17/04* (2013.01)

(58) Field of Classification Search
None
See application file for complete search history.

(56) References Cited

U.S. PATENT DOCUMENTS

| | | | | |
|---|---|---|---|---|
| 4,735,935 A | * | 4/1988 | McAnalley | .......... C07H 15/244 536/123 |
| 2003/0190371 A1 | * | 10/2003 | Graaf | ........................ A61K 8/27 424/642 |
| 2011/0250178 A1 | * | 10/2011 | Brooks | .................. A61Q 19/00 424/195.17 |

FOREIGN PATENT DOCUMENTS

JP     2002238515    *   8/2002

* cited by examiner

*Primary Examiner* — David J Blanchard
*Assistant Examiner* — Sarah J Chickos
(74) *Attorney, Agent, or Firm* — JMB Davis Ben-David

(57) ABSTRACT

Mineral-based composition and methods of use thereof in preventing skin damages, such as in subjects exposed to radiation, are provided.

12 Claims, 5 Drawing Sheets

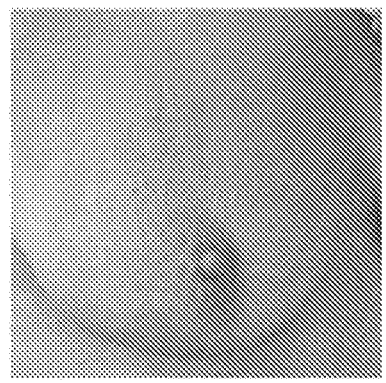
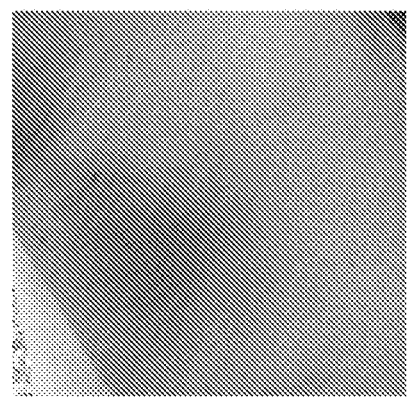
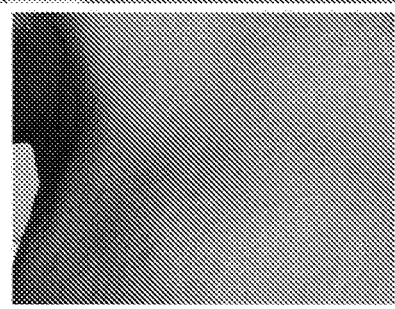
Figure 1A
Figure 1B

MINERAL BASED COMPOSITIONS AND USE THEREOF

CROSS-REFERENCE TO RELATED PATENT APPLICATIONS

This is a Continuation of U.S. application Ser. No. 15/511,579, filed Mar. 15, 2017, which is a U.S. National Phase Application under 35 U.S.C. § 371 of International Patent Application No. PCT/IB15/57264, filed Sep. 21, 2015, and claims priority to U.S. Provisional Application 62/054,040, filed Sep. 23, 2014, which is incorporated by reference in its entirety. The International Application was published on Mar. 31, 2016, as International Publication No. WO 2016/046726 A1.

FIELD OF THE INVENTION

The invention relates to, inter alia, mineral-based formulations and use thereof in preventing skin damages.

BACKGROUND OF THE INVENTION

In higher vertebrates including mammals and particularly in humans, skin is the largest body organ and serves as an important environmental interface, providing a protective envelope that is crucial for homeostasis. The outer layer of skin, the epidermis, is covered by the stratum carenum, a protective layer of dead epidermal skin cells (e.g., keratinocytes) and extracellular connective tissue proteins that is continually being sloughed off as it is replaced by new material pushed up from the underlying epidermal granular cell, spinous cell, and basal cell layers, where continuous cell division and protein synthesis produce new skin cells and skin proteins (e.g., keratin, collagen). Beneath the epidermis lies the dermis, in which dermal fibroblasts elaborate connective tissue proteins (e.g., collagen, elastin, etc.) that assemble into extracellular matrix and fibrous structures that give skin its flexibility, strength and elasticity. Nerves, blood vessels, smooth muscle cells, hair follicles and sebaceous glands are also present in the dermis.

Skin provides physicochemical protection against environmental insults through its barrier function, mechanical strength and imperviousness to water. Epidermal dendritic (Langerhans) cells, and migrating as well as resident white blood cells in the skin (e.g., lymphocytes, macrophages, and mast cells) contribute to immunological protection while pigmented melanocytes in the basal layer absorb potentially harmful ultraviolet (UV) radiation.

Radiation therapy has traditionally been the treatment of choice for locally or regionally advanced cancer, but its therapeutic efficacy is often hindered by limited tolerance of normal tissues and by tumor radio resistance. To improve therapeutic outcome, radiotherapy is frequently combined with chemotherapeutic drugs that are themselves cytotoxic and may sensitize cells to radiation. Radiation may cause severe burns of the skin and surrounding tissue as well as permanent changes in pigmentation.

Further, prolonged exposure to UV radiation, such as from the sun, can lead to the formation of light dermatoses and erythema, as well as increase the risk of skin cancers, such as melanoma, and accelerate skin aging, such as loss of skin elasticity and wrinkling.

There is a need for improved compositions and methods for preventing skin damages such as from exposure to radiation as well as preventing skin cancer reoccurrence.

SUMMARY OF THE INVENTION

The present invention provides mineral-based compositions and methods of use thereof in preventing skin damage. In some embodiments, the compositions and methods described herein are useful for prophylaxis of skin damages due to radiation or laser treatments. In some embodiments, the compositions and methods described herein are useful for prophylaxis of skin cancer.

The present invention is based, in part, on the surprising finding of a unique mineral-based composition useful for preventing damage to the skin including but not limited to burns and cancer such as in subjects exposed to radiation. Without limiting the invention to a particular theory or mechanism of action, the compositions described herein act by allowing the penetration of radiation through the skin (e.g., the epidermis) to the targeted site rather than partially reflecting off the skin and causing damage.

According to one aspect, there is provided a composition comprising:
(i) at least one active ingredient;
(ii) a plurality of minerals selected from: selenium (Se), and zinc (Zn); wherein said selenium and said zinc have a concentration ratio of 1:1 to 10:1 and
(iii) a carrier.

According to another embodiment, the composition further comprises a plurality of minerals selected from potassium (K), calcium (Ca), magnesium (Mg), sulfate (SO4), bromide (Br), manganese (Mn), copper (Cu), sulfur (S), silica (SiO2), iron (Fe), bicarbonate and tellurium (Te), sodium (Na) of less than 1000 mg/l and chloride of less than 500 mg/l.

According to another embodiment, selenium (Se) has a concentration of 40-1000 mg/l, and said zinc (Zn) has a concentration of 4-1000 mg/l.

According to another embodiment, the composition is a hypotonic composition. According to another embodiment, the composition has a pH of less than 7. According to another embodiment, the composition has a pH in the range of 5-7. According to another embodiment, the composition has a pH in the range of 5-6.5.

According to another embodiment, the sodium levels within said composition are less than 600 mg/l. According to another embodiment, the sodium levels within said composition are less than 500 mg/l. According to another embodiment, the sodium levels within said composition are in the range of 100-500 mg/l.

According to another embodiment, the chloride levels within said composition are less than 150 mg/l. According to another embodiment, the chloride levels within said composition are in the range of 50-150 mg/l.

According to another embodiment, said mineral-based composition comprises 50-500 mg/l of sodium, 25000-40000 mg/l potassium, 5000-120000 mg/l calcium, 20000-30000 mg/l magnesium, 50-150 mg/l chloride, 2000-2500 mg/l sulfate, 85-100 mg/l bromide, 5-70 mg/l manganese, 10-50 mg/l copper, 40-1000 mg/l selenium, 4-1000 mg/l zinc, 20-1000 mg/l iron, 3-80 mg/l sulfur, 5-50 mg/l silica, 10-800 mg/l bicarbonate and 0.05-0.5 mg/l tellurium.

According to another embodiment, said composition comprises 0.001-5% of said mineral-based composition. According to another embodiment, said composition comprises 0.01-5% of said mineral-based composition. According to another embodiment, said composition comprises 0.1-5% of said mineral-based composition.

According to another embodiment, said composition comprises 0.01-5% of said active ingredient. According to another embodiment, said active ingredient is uric acid or a derivative thereof. According to another embodiment, said derivative of uric acid is allantoin.

According to another embodiment, said carrier is selected from the group consisting of jojoba oil, coconut oil, aloe vera gel, cocoa butter, lecithin, almond oil, borage oil, canola oil, grape seed oil, olive oil, soybean oil, sunflower oil, wheat germ oil, apricot kernel oil, carrot oil, mango butter, evening primrose oil, black currant oil, avocado oil, macrocrystalline wax, paraffin, petrolatum, petroleum jelly, ozokerite, montan wax, beeswax, lanolin or a derivative, candelilla wax, ouricury wax, carnauba wax, Japan wax, sugarcane wax, cork fiber wax, shea oil, silicone oil, geranium oil and mixtures thereof. According to another embodiment, said carrier is selected from jojoba oil, coconut oil, aloe vera gel, and mixtures thereof.

According to another embodiment, the composition further comprises a compound selected from the group consisting of vitamin E, vitamin A, benzoic acid, benzyl alcohol, cetyl alcohol, citric acid, glycerin, imidazolidinyl urea, isopropyl myristate, methylisothiazolinone, shea butter, sorbitan tristearate and combinations thereof.

According to another embodiment, said composition is formulated as a topical composition. According to another embodiment, said composition is in the form of a cream, an ointment, a gel, lotion, liniment, paste or an emulsion.

According to another embodiment, said composition is characterized by enhanced radiation skin permeability characteristics. According to another embodiment, said composition is useful for preventing or reducing damage to skin exposed to radiation or laser. According to another embodiment, said composition is useful for preventing occurrence or reoccurrence of skin cancer.

According to another aspect, there is provided a method of preventing or reducing skin associated disorders or damages in a subject in need thereof, the method comprises topically applying to the subject an effective amount of the composition described herein. According to another embodiment, said skin associated disorders or damages result from exposure to laser and/or radiation.

According to another embodiment, said subject is undergoing radiotherapy. According to another embodiment, said radiotherapy is external-beam radiation therapy. According to another embodiment, said subject is undergoing laser treatment. According to another embodiment, said skin associated disorders or damages are associated with overexposure to sun.

According to another embodiment, said method comprises applying the composition to the skin of said subject prior to exposure to radiation and/or laser. According to another embodiment, said composition is adsorbed to the skin of the subject prior to exposure to at least one of radiation or laser.

According to another aspect, there is provided a process for preparing a topical formulation comprising the steps of:
(i) providing a mineral-based compositions comprising selenium (Se) and zinc (Zn);
(ii) mixing said mineral-based composition with a wax at a temperature less than 10° C.; and
(iii) mixing the composition of step (ii) with at least one additional ingredient selected from vitamin E, vitamin A, aloe-vera leaf and allantoin at a temperature less than 10° C.

According to another embodiment, said aloe-vera leaf and allantoin are mixed together at a temperature less than 10° C. prior to step (iii).

According to another embodiment, said temperature less than 10° C. is about 5° C. According to another embodiment, said mixing is homogenizing.

According to another embodiment, said selenium and said zinc have a concentration ratio of 1:1 to 10:1.

According to another embodiment, said providing the mineral based composition comprises partially desalinating mineral water. According to another embodiment, said mineral-based composition comprises 50-500 mg/l of sodium, 25000-40000 mg/l potassium, 5000-120000 mg/l calcium, 20000-30000 mg/l magnesium, 50-150 mg/l chloride, 2000-2500 mg/l sulfate, 85-100 mg/l bromide, 5-70 mg/l manganese, 10-50 mg/l copper, 40-1000 mg/l selenium, 4-1000 mg/l zinc, 20-1000 mg/l iron, 3-80 mg/l sulfur, 5-50 mg/l silica, 10-800 mg/l bicarbonate and 0.05-0.5 mg/l tellurium.

According to another embodiment, said formulation has a pH level in the range of 5-7. According to another embodiment, said lowering pH level is by adding citric acid or a derivative thereof to the mineral-based composition of (i).

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE FIGURES

FIGS. 1A-B is a series of photographs of skin of a patient undergoing radiotherapy treated with the composition of the invention (1B), compared to control (1A).

DETAILED DESCRIPTION OF THE INVENTION

Figure 2A:
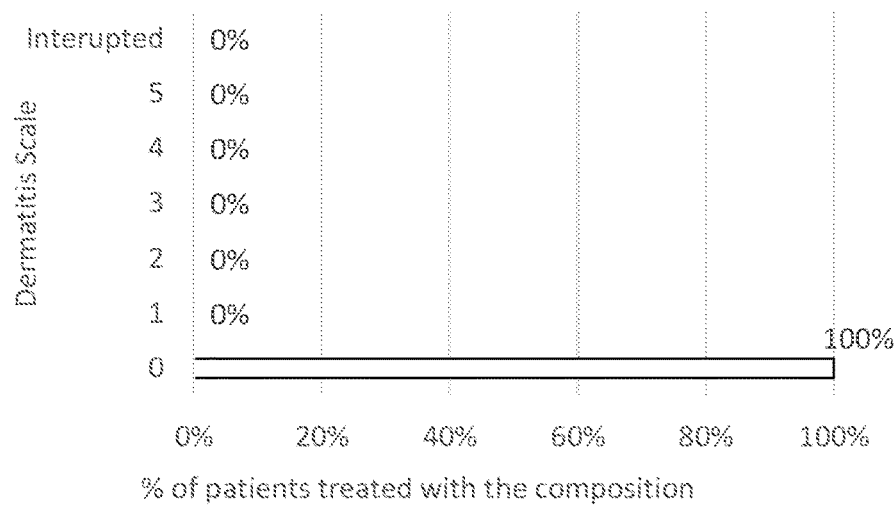
FIGS. 2A-J are bar graphs showing levels of radiation dermatitis in accordance with dermatological scale assessed on a weekly basis in patients treated with the composition for 1 week (A), 2 weeks (B), 3 weeks (C), 4 weeks (D) and 5 weeks (E) and patients treated with the standard treatment for 1 week (F), 2 weeks (G), 3 weeks (H), 4 weeks (I) and 5 weeks (J).

The present invention provides compositions comprising a unique constitution of minerals and processes for producing said compositions. The invention further provides methods for preventing skin damage by applying the disclosed composition to a skin of a subject in need thereof.

According to a first aspect, the composition of the present invention comprises: at least one active ingredient; selenium (Se), and zinc (Zn); and a carrier.

In some embodiments, the selenium (Se), and the zinc (Zn) have a concentration ratio of 1:1 to 1:10. In some embodiments, the selenium (Se), and the zinc (Zn) have a concentration ratio of 1:1 to 1:9. In some embodiments, the selenium (Se), and the zinc (Zn) have a concentration ratio of 1:1 to 1:8. In some embodiments, the selenium (Se), and the zinc (Zn) have a concentration ratio of 1:2 to 1:8. In some embodiments, the selenium (Se), and the zinc (Zn) have a concentration ratio of 1:1 to 1:5. In some embodiments, the selenium (Se), and the zinc (Zn) have a concentration ratio of 1:2 to 1:6. In some embodiments, the selenium (Se), and the zinc (Zn) have a concentration ratio of 1:3 to 1:6.

In some embodiments, the composition comprises 40-1000 mg/l selenium. In some embodiments, the composition comprises 4-1000 mg/l zinc.

In some embodiment the composition further comprises a plurality of minerals selected from: manganese (Mn), copper (Cu) and iron (Fe). In some embodiments, the composition further comprises a plurality of minerals selected from potassium (K), calcium (Ca), magnesium (Mg), sulfate (SO4), bromide (Br), manganese (Mn), copper (Cu), sulfur (S), silica (SiO2), iron (Fe), bicarbonate and tellurium (Te), sodium (Na) and chloride (Cl).

In some embodiments, the composition includes a plurality of minerals selected from zinc selenium manganese (Mn), copper (Cu) and iron (Fe). In some embodiments, the composition further comprises a plurality of minerals selected from potassium (K), calcium (Ca), magnesium (Mg), sulfate (SO4), bromide (Br), manganese (Mn), copper (Cu), sulfur (S), silica (SiO2), iron (Fe), bicarbonate and tellurium (Te), sodium (Na) and chloride (Cl)) and/or derivatives thereof. As used herein the term "derivatives" refers to oxidized forms of the minerals, such as for a non-limiting example ZnO which is an oxidized derivative of zinc, solid solutions of the mineral, organic composition of the minerals, such as for a non-limiting example selenium methionine which is an organic composition of selenium, inorganic composition of the minerals, and other derivatives.

According to some embodiments, the composition is a hypotonic composition. According to some embodiments, the composition has a pH of less than 7. According to some embodiments, the composition has a pH in the range of 5-7. According to another embodiment, the composition has a pH in the range of 5-6.5. According to another embodiment, the composition has a pH of less than 8. According to another embodiment, the composition has a pH in the range of 5-8. According to another embodiment, the composition has a pH in the range of 1-8. According to another embodiment, the composition has a pH in the range of 1-5. According to another embodiment, the composition has a pH in the range of 1-2. According to another embodiment, the composition has a pH in the range of 1-1.8.

In some embodiments, a PH adaptor may be added to the composition in order to maintain a specific pH range. The PH adaptor can be any material capable of adjusting PH values, where the types and molecular weight of the PH adaptor are without particular limitation.

According to another embodiment, the sodium levels within said composition are less than 1000 mg/l and chloride of less According to another embodiment, the sodium levels within said composition are less than 600 mg/l. According to another embodiment, the sodium levels within said composition are less than 500 mg/l. According to another embodiment, the sodium levels within said composition are in the range of 100-500 mg/l.

According to another embodiment, the chloride levels within said composition are less than 500 mg/l. According to another embodiment, the chloride levels within said composition are less than 150 mg/l. According to another embodiment, the chloride levels within said composition are in the range of 50-150 mg/l.

According to another embodiment, said mineral-based composition comprises 50-500 mg/l of sodium, 25000-40000 mg/l potassium, 5000-120000 mg/l calcium, 20000-30000 mg/l magnesium, 50-150 mg/l chloride, 2000-2500 mg/l sulfate, 85-100 mg/l bromide, 5-70 mg/l manganese, 10-50 mg/l copper, 40-1000 mg/l selenium, 4-1000 mg/l zinc, 20-1000 mg/l iron, 3-80 mg/l sulfur, 5-50 mg/l silica, 10-800 mg/l bicarbonate and 0.05-0.5 mg/l tellurium.

According to another embodiment, said composition comprises 0.001-5% of said mineral-based composition. According to another embodiment, said composition comprises 0.01-5% of said mineral-based composition. According to another embodiment, said composition comprises 0.1-5% of said mineral-based composition. As exemplified herein below, the composition described herein was topically applied to subjects prone to skin cancer reoccurrence. Surprisingly, reoccurrence of skin cancer did not reoccur over time. In some embodiments, the composition described herein is useful for preventing or reducing the occurrence of skin cancer, including, but not limited to melanoma, basal cell carcinoma, squamous cell carcinoma, and merkel cell carcinoma.

In additional embodiments, the composition described herein is useful for preventing skin damage which results for example from radiotherapy that is given to cancer patients. The composition described herein is useful for preventing skin damage which takes place due to laser, radiation or UV rays that are used for therapeutic and/or cosmetic purposes.

In some embodiments, topically applying the compositions described herein results in enlargement of skin pores, thereby enhancing penetration of radiation through the skin to the targeted site rather than partially reflecting off the skin and causing damage.

As exemplified herein below, topically applying the composition to the skin of a patient prior to undergoing radiation treatment remarkably reduced the damage to the skin of said patient. With regard to radiotherapy or laser treatments, current treatments are often discontinued due to skin damage. In advantageous embodiments, the composition and method described herein allow treatment (e.g., radiotherapy) over longer periods of time, thereby increasing the survival rates of cancer patients.

As described above, an adverse effect commonly seen in radiation or laser treatment (e.g., for treating cancer or for hair removal) is burns caused by partial absorption of heat or energy by the surrounding skin, which leads to skin damage including but not limited to burns, pigmentation and scars.

In some embodiments, the topical composition described herein is applied to the skin before the treatment or exposure to radiation or laser. In embodiments wherein the composition is applied for prevention of skin damage due to exposure to radiation or laser, the topical composition is applied at least 30 seconds, at least 1 minute, at least 5 minutes, at least 10 minutes, at least 15 minutes, at least 20 minutes, at least 30 minutes, at least 1 hour or at least 2 hours before said exposure to radiation or laser. In some embodiments, the composition is applied to the area of the skin which is to be exposed to the radiation or laser. A used herein, the "area of the skin" exposed to radiation or laser includes skin surrounding the particular site of exposure, such as in a radius of at least 1 cm, at least 2 cm, at least 3 cm, at least 4 cm, at least 5 cm, at least 6 cm, at least 7 cm, at least 8 cm, at least 9 cm, at least 10 cm from the site of exposure.

In some embodiments, the composition may be applied at least 24 hours prior to exposure to radiation. In some embodiments, the composition may be applied at least 16 hours prior to exposure to radiation. In some embodiments, the composition may be applied at least 12 hours prior to exposure to radiation.

In some embodiments, the topical composition described herein is applied to the skin of a human. In some embodiments, the topical composition described herein is applied to the skin of a mammal. In some embodiments, the topical composition described herein is applied to the skin of an animal. Non-limiting examples of subjects to be treated by the topical composition described herein include human, horse, cow, camel, goat, sheep, dog, cat, non-human primate, mouse, rat, rabbit, hamster, guinea pig, pig.

Unless otherwise indicated, the term "skin" means that outer integument or covering of the body, consisting of the dermis and the epidermis and resting upon subcutaneous tissue.

The terms "prevent" or "preventing" as used herein refers to prophylactic or preventative measures, wherein the object is to prevent or slow down (lessen) an undesired skin condition. The term "reducing" includes the administration of a compound of the present invention to prevent the onset of the symptoms, alleviating the symptoms, or eliminating the skin condition. By "reduces" is meant a negative alteration of at least 10%, 25%, 50%, 75%, or 100%.

As used herein, the term "skin damage" includes burns, ulcers, irritation, pain, itching fine and coarse wrinkles, pigmentation including mottled pigmentation, sallowness (i.e., yellow discoloration of the skin), freckles, as well as telangiectasias (i.e., dilation of small blood vessels under the skin) and elastosis (i.e., destruction of the elastic tissue in the skin). In some embodiments, said skin damage or disorder is radiation dermatitis or radiodermatitis.

Radiotherapy

Radiation therapy works by directing ionizing radiation into the area being treated with the goal of damaging the genetic material of cancerous cells thereby making it impossible for these cells to divide. Accordingly, radiotherapy is an important tool in the fight against cancer and is used in the treatment many cancer patients. Other terms for radiotherapy include radiation therapy, x-ray therapy, electron beam therapy, cobalt therapy, or irradiation.

Radiotherapy is especially useful in cases where surgical removal of the cancer is not possible, where surgery might debilitate the patient, or where surgical debulking of the tumor has not absolutely removed all cancerous tissue. Radiotherapy is routinely used following surgery to destroy any cancer cells that were not removed by surgery. Further uses of radiotherapy are prior to surgery where it can "shrink" a previously inoperable tumor down to a manageable size to enable surgical excision.

Radiation therapy can also be used to help relieve symptoms of advanced cancer (such as bleeding or pain), even if a cure is not possible. Over one-third of the practice of radiation therapy is palliative. The typical intent of palliative treatment is to relieve pain quickly and maintain symptom control for the duration of the patient's life. Accordingly, treatment is usually tailored to the patient's clinical condition and overall prognosis. Palliative treatment is often complementary to analgesic drug therapies and may enhance their effectiveness because it can directly target the cause of pain.

Specifically, radiotherapy can be used to treat localized solid tumors, such as cancers of the skin, head and neck, brain, breast, prostate, cervix, and the like. Radiation therapy can also be used to treat cancers of the blood-forming cells and lymphatic system including leukemia and lymphoma respectively, and the like. Skin cells in the vicinity of the radiation or in the path of the radiation can be protected using the present invention.

Radiation Forms and Dosage

External beam radiation therapy commonly uses photons, which are sometimes called "packets of energy," to treat cancer. It is an object herein to ameliorate the negative effects of all radiotherapy regardless of the form of the photon or particle, including x-rays, gamma rays, UV rays including UV-A, UV-B and UV-C, neutrons, protons, and electrons including beta particles and the like.

X-rays are a very common form of radiation used in radiotherapy. Gamma rays are another form of photons used in radiotherapy. Gamma rays can be produced spontaneously as certain elements (such as radium, uranium, and cobalt 60), which release radiation as they decompose, or decay. Each element decays at a specific rate and can give off energy in the form of gamma rays and other particles. Typically x-rays and gamma rays have the same general effect on cancer cells.

External beam radiation therapy can be delivered by means of a linear accelerator. Typically, linear accelerators use powerful generators to create the high energy rays for external beam radiation therapy. Generally, linear accelerators are capable of producing x-rays at various energies. The linear accelerator can include a special set of lead shutters, called collimators, which focus and direct the rays to the tumor. The linear accelerator can be a large "L-shaped" design which allows it to rotate and deliver radiation from all angles. Multiple angles allow the maximum amount of radiation to be delivered to the tumor while delivering a minimal amount of radiation to the surrounding healthy tissue. The formulations and methods described herein can be used in conjunction with collimators or other devices and methods that limit radiation exposure to normal cells.

Formulations and methods described herein are capable of ameliorating the effects of radiotherapy on skin cells. For example, the compositions and methods can ameliorate the effects of local-field radiation and wide-field radiation. Local field radiation relates to a narrow beam of radiation directed at the specific metastatic site or sites. Customarily, local field radiation has tended to be used for patients with a long life expectancy and fewer metastatic sites. In contrast, wide-field radiation employs a larger field of radiation and is often used to treat patients with a shorter life expectancy and multiple metastatic pain-causing sites.

Radiotherapy dosage is measured by the scientific unit rad (radiation absorbed dose) which is a radiation energy dose equal to energy of 100 ergs per gram of irradiated material. A patient who receives radiation therapy as a treatment for cancer can receive several thousand rads over a very short period of time (weeks or months). In contrast, a typical scanning x-ray contains far fewer rads. For example, modern mammography systems used to take x-ray images of the breast use approximately 0.1 to 0.2 rad dose per x-ray.

In general, radiation therapy is a local treatment. It typically affects the cells in the treated area. However, as mentioned above, in addition to damaging cancer cells, radiation can also damage normal cells located in the treated area and particularly skin cells in the radiation path. Radiation side effects are typically restricted to the radiation portal and can be classified as acute, occurring during or immediately after the course of radiation therapy, or late, occurring months to years later. Acute radiation effects are more prominent with radiation schedules that deliver high total doses of radiation with small daily fractions; they generally begin at the end of the second week of therapy. Acute radiation effects, occurring at skin surfaces, usually consist of an inflammatory response such as skin erythema or pigmentation. Late radiation effects may arise without any preceding acute reactions. Fibrosis is the most common type of late radiation injury and can be observed in many types of tissue, including skin.

Other skin conditions caused by radiation therapy include dry and moist desquamation. Dry desquamation, which is characterized by dry and flaky skin and pruritus in the area of irradiation. Moist desquamation, is characterized by sloughing of the epidermis, exposing the moist, raw, dermis layer of the skin.

One objective described herein is to ameliorate the negative effects of radiation therapy on normal skin cells, regardless of whether the effect is acute or late.

In some embodiments, radiation includes ultraviolet (UV) rays and particularly UV-A and UV-B radiation such as from the sun. Ultraviolet radiation between 290 nm and 320 nm ("UV-A") has been known to rapidly produce damage to the human skin. Also, the human skin has been known to be affected by UV radiation between 320-400 nm ("UV-B").

In some embodiments, laser includes laser beam used in laser therapy for cosmetic skin treatments and hair removal. Currently, 1064 nm wavelength is approved by FDA for permanent hair reduction.

The formulation of the composition may be applied before exposure to radiotherapy. The composition may be applied during one to two weeks before radiotherapy, one-three times daily.

Pharmaceutical Compositions

In some embodiments, there is provided pharmaceutical compositions comprising a therapeutically effective amount of an active ingredient (such as allantoin), a plurality of minerals and a pharmaceutically acceptable carrier.

As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio. For example, the term "pharmaceutically acceptable" can mean approved by a regulatory agency of the Federal or a state government or listed in the U. S. Pharmacopeia or other generally recognized pharmacopeia for use in animals, and more particularly in humans.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician.

The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as jojoba oil, coconut oil, aloe-vera oil, peanut oil, soybean oil, mineral oil, sesame oil and the like, polyethylene glycols, glycerine, propylene glycol or other synthetic solvents.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose may also envisioned.

In some embodiments, the pharmaceutical composition is water based composition. As used herein the term "water based" refers to a pharmaceutical composition whose primary solvent is water.

For topical application, a composition of the present invention or derivative thereof can be combined with a pharmaceutically acceptable carrier so that an effective dosage is delivered, based on the desired activity. The carrier can be in the form of, for example, and not by way of limitation, an ointment, cream, gel, paste, foam, aerosol, suppository, pad or gelled stick.

As used herein, "topical application" means directly laying on or spreading on outer skin.

Pharmaceutical compositions according to embodiments of the invention may contain 0.01%-50%, 0.05%-50% of the active components(s) of this invention, 0.1%-25%, 0.1%-5% or 0.1%-1%. In any event, the composition or formulation to be administered may contain a quantity of active components according to embodiments of the invention in an amount effective to reduce or prevent skin conditions as described herein.

According to another embodiment, said active ingredient is uric acid or a derivative thereof. According to another embodiment, said derivative of uric acid is allantoin.

Encompassed within this disclosure is all forms of allantoin, or a salt thereof, including, but not limited to, crystals, polymorphs, clathrates, solvates, hydrates, amorphous forms, co-crystals, and anhydrous forms.

In some embodiments, pharmaceutical compositions according to embodiments of the invention may contain 0.01%-50%, 1%-3%, 0.1%-10% or 0.1%-5% allantoin. In some embodiments, pharmaceutical compositions according to embodiments of the invention may contain 0.01%-3%, 1%-3%, 0.1%-3% or 0.1%-1% allantoin.

Embodiments of the present disclosure also relate to the salts of allantoin. The acids which are used to prepare the salts of the aforementioned compound are those which form non-toxic salts, i.e., salts containing pharmacologically acceptable anions, such as the hydrochloride, acetate, trifluoroacetic acid, tosylate, picrate, hydrobromide, hydroiodide, nitrate, sulfate, bisulfate, phosphate, acid phosphate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate salts.

The composition may further comprise one or more pharmaceutically acceptable excipients comprising lipids, oils, emulsifiers, initiators, pH adjusting agents, thickening agents, emollients, humectants, preservatives, antioxidants, and chelating agents.

The composition may further comprise one or more of the ingredients selected from: Isopropyl myristate, Aloe barbadensis leaf extract (e.g., juice), Glyceryl Stearate, cetyl alcohol, sweet almond oil, Butyrospermum Parkii, Propylene glycol, polyethylene glycol (PEG) 40 Stearate, Jujuoba seed oil (*Simmondsia chinensis*), Ethylhexyl methoxycinnamate, glycerin, Sorbitan Tristearate, Tocopherol acetate (Vitamin E acetate), Butyl Methoxydibenzoylmethane, Germanium oil (or any other natural fragrance), Imidazolidinyl urea, Dehydroacetic acid, Benzoic acid, sorbic acid and benzyl alcohol.

In some embodiments, the formulation may include an emulsifying agent, or emulsifier. In embodiments, the emulsifier may be, for example, sodium lauryl sulfate, white waxes such as beeswax or paraffin wax, sesquioleates such as sorbitan sesquioleate or polyglyceryl-2-sesquioleate, ethoxylated esters of derivatives of natural oils such as the polyethoxylated ester of hydrogenated castor oil, silicone emulsifiers such as silicone polyols, anionic emulsifiers, fatty acid soaps such as potassium stearate and fatty acid sulphates like sodium cetostearyl sulphate, ethoxylated fatty alcohols, sorbitan esters, ethoxylated sorbitan esters, ethoxylated fatty acid esters such as ethoxylated stearates, ethoxylated mono, di-, and triglycerides, non-ionic self-emulsifying waxes, ethoxylated fatty acids, methylglucose esters such as polyglycerol-3 methyl glucose distearate, and combinations thereof. Various emulsions suitable for embodiments described herein and methods for preparing such emulsions are well known in the art and are described in, for example, Remington's Pharmaceutical Sciences, Mack Publishing Co., Easton, Pa., USA, which is hereby incorporated by reference in its entirety. In some embodiments, the formulation may include an emulsifier in an amount from about 1% to about 15%, and in other embodiments, the formulation may include from about 1% to about 10%, or from about 1% to about 5% emulsifier. If more than one emulsifier is used, the formulation may include from about 1% to about 5% or from about 1.5% to about 3% by weight of the formulation of each emulsifier.

In some embodiments, the formulations described herein may include one or more surfactants. Such embodiments are not limited by type of surfactant used; for example, in some embodiments, the one or more surfactants may be anionic surfactants such as alkyl sulfates, alkylether sulfates, alkylsulfonates, alkylaryl sulfonates, alkyl succinates, alkyl sulfosuccinates, N-alkoylsarcosinates, acyl taurates, acyl isethionates, alkyl phosphates, alkyl ether phosphates, alkyl ether carboxylates, .alpha.-olefinsulfonates, and the alkali metal and alkaline earth metal salts and ammonium and triethanolamine salts thereof. Such alkyl ether sulfates, alkyl ether phosphates and alkyl ether carboxylates can have between 1 and 10 ethylene oxide or propylene oxide units, and in some embodiments, 1 to 3 ethylene oxide units, per molecule. More specific examples include, but are not limited to, sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzene sulfonate, triethanolamine dodecylbenzenesulfonate. In other embodiments, the one or more surfactants may be amphoteric surfactants such as, for example, alkylbetaines, alkylamidopropylbetaines, alkylsulfobetaines, alkylglycinates, alkylcarboxyglycinates, alkylamphoacetates or alpha-propionates, alkylamphodiacetates or alpha-dipropionates, and more specifically, cocodimethylsulfopropylbetaine, lauryl betaine, cocamidopropylbetaine or sodium cocamphopropionate.

In certain embodiments, the one or more surfactants may be non-ionic surfactants such as, for example, the reaction products of aliphatic alcohols or alkylphenols having 6 to 20 carbon atoms in a linear or branched alkyl chain with ethylene oxide and/or propylene oxide where the alkylene oxide may be from about 6 moles to about 60 moles per mole of alcohol. In particular embodiments, non-ionic surfactants may include alkyl amine oxides, mono- and dialkylalkanolamides, fatty acid esters of polyethylenenglycols, ethoxylated fatty acids amides, saturated fatty acid alcohols reacted with ethylene oxide, alkyl polyglycosides, and sorbitan ether esters, and in some embodiments, the non-ionic surfactant may be ceteareth-2, ceteareth-3, ceteareth-4, ceteareth-5, ceteareth-6, ceteareth-7, ceteareth-8, ceteareth-9, ceteareth-10, ceteareth-11, ceteareth-12, ceteareth-13, ceteareth-14, ceteareth-15, ceteareth-16, ceteareth-17, ceteareth-18, ceteareth-20, ceteareth-22, ceteareth-23, ceteareth-24, ceteareth-25, ceteareth-27, ceteareth-28, ceteareth-29, ceteareth-30, ceteareth-33, ceteareth-34, ceteareth-40, ceteareth-50, ceteareth-55, ceteareth-60, ceteareth-80, ceteareth-100, and the like or combinations thereof, or one or more ceteareth in combination with a fatty acid alcohol such as stearyl alcohol, oleyl alcohol, linoleyl alcohol, arachidyl alcohol, cetyl alcohol, and the like. The surfactant of various embodiments may make up from about 0.1% to about 20% by weight of the formulation and in some embodiments, from about 0.5% to about 20% by weight of the formulation. In embodiments in which more than one surfactant is provided in the formulation, each surfactant may be from about 0.5% to about 10% by weight of the formulation, and in some embodiments, each surfactant of the formulation may be from about 0.5% to about 6% by weight of the formulation.

In some embodiments, the formulation may comprise emollients in an amount from about 8% to about 30% by weight of the formulation. In formulations that include more than one emollient, each emollient may be provided at about 0.05% to about 15% by weight of any one emollient. Emollients are well known in the art and are listed, for example, the International Cosmetic Ingredient Dictionary, Eighth Edition, 2000, which is hereby incorporated by reference in its entirety. In certain embodiments, the emollient may be fatty esters, fatty alcohols, or combinations thereof including, but not limited to, diisopropyl adipate, oleyl alcohol, lanolin, isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, polyoxypropylene (5) poloxyethylene (20) cetyl ether (PPG-5-Ceteth-20), 2-ethylhexyl isononoate, 2-ethylhexyl stearate, $C_{12}$ to $C_{16}$ fatty alcohol, $C_{12}$ to $C_{16}$ fatty alcohol lactate, isopropyl lanolate, 2-ethyl-hexyl salicylate, and combinations thereof. In some embodiments, the one or more emollients may be a combination of fatty alcohols. In certain embodiments, the one or more emollients may be 1-hexadecanol, acetylated lanolin, behenocyl dimethicone, $C_{12}$-$C_{15}$ alkyl benzoate, cetearyl octanoate, cocoglycerides, dicaprylate/dicaprate dimethicone copolyol, dimethiconol, dioctyl adipate, glyceryl stearate, isocetyl alcohol, isohexadecane, isopentylcyclohexanone, isopropyl palmitate, lauryl lactate, mineral oil, methoxy peg-22/dodecyl glycol copolymer, myristyl lactate, ocryldodecyl neopentanoate, octyl cocoate, octyl palmitate, octyl stearate, octyldodecyl neopentanoate, polyglyceryl-4 isosterate, polyoxyl 40 stearate, polyoxymethylene urea, potassium sorbate, propylene glycol, propylene glycol isoceth-3 acetate, and propylene glycol myristyl ether acetate. In some embodiments, the emollient may be a high molecular weight saturated and unsaturated fatty alcohol such as, but not limited to, carbitol, lauryl alcohol, myristyl alcohol, cetyl alcohol, isocetyl alcohol, stearyl alcohol, isostearyl alcohol, hydroxystearyl alcohol, oleyl alcohol, ricinoleyl alcohol, behenyl alcohol, erucyl alcohol, 2-octyldodecanyl alcohol, cetearyl alcohol, lanolin alcohol, or the like. In particular embodiments, the emollient may be selected from cetyl alcohol, stearyl alcohol, lanolin oil, cod liver oil, or a combination thereof. In some embodiments, the formulation may comprise an emollient such as, without limitations, cetyl alcohol in an amount from about 2% to about 6%, stearyl alcohol in an amount from about 1% to about 3%, lanolin in an amount from about 5% to about 15%, cod liver oil in an amount from about 0.05% to about 5% or combinations thereof.

In some embodiments, the formulation may include one or more viscosity modifiers. In some embodiments, the formulation may comprise from about 1% to about 10% or from about 1% to about 6% of each viscosity modifier. The viscosity modifier of such embodiments may generally include a high molecular weight compound such as, for example, carboxyvinyl polymer, carboxymethyl cellulose, polyvinyl pyrrolidone, hydroxyethyl cellulose, methyl cellulose, natural gum such as gelatin and tragacanth gum, and various alcohols such as polyvinyl alcohol. In other embodiments, the viscosity modifier may include ethanol or isopropyl alcohol. In some embodiments, the viscosity modifier may be a high molecular weight saturated and unsaturated fatty alcohol such as, but not limited to, carbitol, lauryl alcohol, myristyl alcohol, cetyl alcohol, isocetyl alcohol, stearyl alcohol, isostearyl alcohol, hydroxystearyl alcohol, oleyl alcohol, ricinoleyl alcohol, behenyl alcohol, erucyl alcohol, 2-octyldodecanyl alcohol, cetearyl alcohol, lanolin alcohol, and the like, and in certain embodiments, the viscosity modifier may be cetyl alcohol, stearyl alcohol or a combination thereof. In some embodiments, the formulation may comprise a viscosity modifier such as, without limitations, cetyl alcohol in an amount from about 2% to about 6%, stearyl alcohol in an amount from about 1% to about 3%, or combinations thereof.

Formulations of embodiments herein may further include a preservative. For example, preservatives useful in embodiments may include, but are not limited to, pentylene glycol, ethylene diamine tetra acetate (EDTA) and its salts, chlorhexidine and its diacetate, dihydrochloride, digluconate derivatives, 1,1,1-trichloro-2-methyl-2-propanol, parachlorometaxylenol, polyhexamethylenebiguanide hydrochloride, dehydroacetic acid, diazolidinyl urea, 2,4-dichlorobenzyl alcohol, 4,4-dimethyl-1,3-oxazolidine, formaldehyde, glutaraldehyde, dimethylidantoin, imidazolidinyl urea, 5-chloro-2-methyl-4-isothiazolin-3-one, ortho-phenylphenol, benzyl alcohol, benzoic acid and its salts, 4-hydroxybenzoic acid and its methyl-, ethyl-, propyl-, isopropyl-, butyl-, isobutyl-esters (parabens), methylparaben, propylparaben, isopropylparabens, isobutylparabens, butylparabens, ethylparaben, trichlosan, 2-phenoxyethanol, phenyl mercuric acetate, quaternium-15, methylsalicylate, salicylic acid and its salts, sorbic acid and its salts, iodopropanyl butylcarbamate, calcium sorbate, zinc pyrithione, 5-bromo-5nitro-1,3-dioxane, 2-bromo-2-nitropropane-1,3-diol, sulfites, bisulfites, and benzalkonium chloride, phenoxyethanol, 2-phenoxyethanol, chloroxylenol, diazolidinyl urea, and combinations thereof. In certain embodiments, the formulation may include a combination of methylparaben and propylparaben. Preservatives may be provided in any concentration known in the art. For example in some embodiments, the formulation may include preservatives in an amount from about 0.01% to about 3% by weight; and, in embodiments, the formulation may include from about 0.05% to about 1% or from about 0.05% to about 0.5% by weight of any one preservative.

The formulations of various embodiments may further include a chelating agent or combination of chelating agents. Examples of the chelating agents useful in various embodiments include, but are not limited to, alanine, sodium polyphosphate, sodium methaphosphate, citric acid, phosphoric acid, tartaric acid, ethylenediamine tetra acetic acid (Edetate, EDTA) and derivatives and salts thereof, dihydroxyethyl glycine, and combinations thereof. In particular embodiments, the chelating agent may be tetrasodium EDTA. The chelating agents may be provided in any effective amount. For example, in some embodiments, the formulation may include from about 0.01% to about 2% by weight chelating agent, and in other embodiments, the formulation may include from about 0.05% to about 0.5% or from about 0.05% to about 0.35% by weight chelating agent.

The formulations of certain embodiments may include one or more antioxidants. Numerous antioxidants are known in the art, and any such antioxidant may be used to prepare the formulations described herein. Examples of suitable antioxidants include, but are not limited to, amino acids such as glycine, histidine, tyrosine, trytophan and derivatives thereof, imidazoles such as urocanic acid and derivatives thereof, peptides, such as D,L-carnosine, D-carnosine, L-carnosine and derivatives thereof such as anserine, carotinoids, carotenes such as alpha.-carotone, beta.-carotene, lycopene, and derivatives thereof, chlorogenic acid and derivatives thereof, lipoic acid and derivatives thereof such as dihydrlipoic acid, aurothioglycose, propylthiouracil and other thiols such as thioredoxin, glutathione, cysteine, cystine, cystamine and glycosyl, N-acetyl, methyl, ethyl, propyl, amyl, butyl, lauryl, palmitoyl, oleyl, .alpha.-linoleyl, cholesteryl and glyceryl esters and salts thereof, dilauryl thiodipropionate, distearyl thiodipropionate, thiodipropionic acid and derivatives thereof such as esters, ethers, peptides, lipids, nucleotides, nucleosides, and salts, sulfoximine compounds such as buthionine sulfoximines, homocysteine sulfoximine, buthionine sulfones, penta-, hexa-, hepta-thionine sulfoximine, unsaturated fatty acids and derivatives thereof such as .alpha.-linolenic acid, linoleic acid, oleic acid, folic acid and derivatives thereof, ubiquinone and ubiquinol and derivatives thereof, vitamin C and derivatives thereof such as ascorbyl palmitate, magnesium ascorbyl phosphate, ascorbyl acetate, tocopherals and derivatives such as vitamin E acetate, vitamin A and derivatives such as vitamin A palmitate, vitamin B and derivatives thereof, coniferyl benzoate of benzoin resin, rutinic acid and derivatives thereof, alpha-glycosylrutin, ferulic acid, furfurylidene glucitol, carnosine, butyl hydroxytoluene, trihydroxy-butyrophenone, uric acid and derivatives thereof, mannose and derivatives thereof, superoxide dismutase, zinc and derivatives thereof such as ZnO, $ZnSO_4$, selenium and derivatives thereof such as selenium methionine, stilbene and derivatives thereof such as stilbene oxide, trans-stilbene oxide and the like. In some embodiments, the antioxidants may include vitamin B, nordihydroguaiaretic acid, butylated hydroxyanisole (BHA), butylated hydroxytoluene (BHT), propyl gallate, erythorbate acid, sodium erythorbate, ascorbir palmitate, and ascorbir stearate, butyl hydroxyanisole, and gallic esters, and in particular embodiments, the one or more antioxidants may include BHT. The antioxidant may be provided in any suitable amount. For example in some embodiments, one or more antioxidants may be from about 0.001% to about 3% by weight of the formulation, and in other embodiments, the one or more antioxidants may be from about 0.01% to about 1% by weight of the formulation or from about 0.05% to about 1% by weight of the formulation.

In some embodiments, the formulation may include a solubilizing agent. In embodiments, the solubilizers may be, for example, hydrochloric acid, sodium hydroxide, glycine, cyclodextrin, liquid paraffin, hydrogenated castor oil, ethanol, glycerin, propylene glycol, dilute hydrochloric acid, hydrogenated oils, purified water, physiological saline, water for injection, Macrogol 4000, Polysorbate 80, or a combination thereof. In particular embodiments, the solubilizing agent may be propylene glycol, glycerin or a combination thereof. In embodiments, the solubilizing agent comprises from about 1% to about 20%, from about 1% to about 10% or from about 2% to about 8% by weight of the formulation.

In some embodiments, the formulation may include one or more skin conditioners. Common skin conditioners include, for example, mineral oil, petrolatum, aliphatic alcohols, lanolin and its derivatives, fatty acids, glycol fatty acids, sugars, glycerin, propylene glycol, sorbitols, and polyethylene glycols, vitamins and herbal derivatives. Additional skin conditioners can be found in CTFA Cosmetic Ingredient Handbook, 1st Ed., 1988, which is hereby incorporated herein by reference in its entirety. In some embodiments, the one or more skin conditioners may include, but are not limited to, humectants, such as fructose, glucose, glycerin, propylene glycol, glycereth-26, mannitol and urea, pyrrolidone carboxylic acid, hydrolyzed lecithin, coco-betaine, cysteine hydrochloride, glutamine, polyoxypropylene (15) polyoxyethylene (PPG-15), sodium gluconate, potassium aspartate, oleyl betaine, thiamine hydrochloride, sodium laureth sulfate, sodium hyaluronate, hydrolyzed proteins, hydrolyzed keratin, amino acids, amine oxides, water-soluble derivatives of vitamins A, E and D, amino-functional silicones, ethoxylated glycerin, .alpha.-hydroxy acids and salts thereof, water-soluble fatty oil derivatives, such as PEG-24 hydrogenated lanolin, almond oil, grape seed oil and castor oil; numerous other water-soluble skin conditioners listed, and combinations thereof. In certain embodiments, the skin conditioners may include lanolin or lanolin derivatives, caprylic capric/triglyceride, diisopropyl adipate, and combinations thereof. Skin conditioners may be provided to various embodiments in any amount known in the art, and the amount of skin conditioner provided may vary depending upon the type of skin condition or combination of skin conditioners used. In general, the formulations of embodiments may include a conditioner in an amount from about 1% to about 30% by weight of the formulation or from about 1% to about 25% by weight of the formulation.

The pH of various embodiments may be of neutral to mildly acidic pH to allow for comfortable application to a subject's skin. For example, in various embodiments, the pH of the formulations may be from about 2.5 to about 7.0, from about 4.0 to about 7.0, or from about 4.0 to about 5.5 at room temperature. In other embodiments, the pH of such formulations may be about 4.0 to about 5.0 at room temperature. In other embodiments, the pH of such formulations may be about 4.0 to about 8.0 at room temperature. Any components or combination of components known and useful in the art may be used to achieve an appropriate pH such as, for example, pH regulators including, but not limited to, lactic acid, citric acid, sodium citrate, glycolic acid, succinic acid, phosphoric acid, monosodium phosphate, disodium phosphate, oxalic acid, dl-malic acid, calcium carbonate, sodium hydroxide and sodium carbonate, sodium hydrogen carbonate, and ammonium hydrogen carbonate. In particular embodiments, the formulation may include, for example, citric acid or lactic acid as a pH modifier. In embodiments, the pH modifier may comprise from about 0.01% to about 1%, from about 0.05% to about 0.5%, from about 0.06% to about 0.15%, from about 0.06% to about 0.11%, or from about 0.06% to about 0.1% by weight of the formulation.

In embodiments, the formulation may further comprise a solvent. In some embodiments, the solvent may include one or more ingredients therein, with water being preferred in certain embodiments. Generally, the quantity of water used as a solvent may depend on the various other ingredients used. The solvent may be present in certain embodiments in a range of from about 10% to about 95% by weight, with certain embodiments including from about 40% to about 90%, from about 42% to about 87%, from about 42% to about 80%, from about 42% to about 75%, from about 42% to about 70%, or from about 42% to about 68% by weight of the formulation. The exact quantity of solvent may be dependent on the form of the product. For example, a product in lotion form may in certain preferred embodiments include more water than a product in spray form and a product in cream or butter form may include less water than a product in spray form. Deionized water is generally preferred. Other suitable solvent materials may also be used.

In some embodiments, a process for preparing a topical formulation comprises the steps of:
 (i) providing a mineral-based compositions comprising selenium (Se) and zinc (Zn);
 (ii) mixing said mineral-based composition with a wax; and
 (iii) mixing the composition of step (ii) with at least one additional ingredient selected from vitamin E, vitamin A, aloe-vera leaf and allantoin at a temperature less than 10° C.

In some embodiments, mixing steps (ii) and or (iii) are performed at a temperature of less than 10° C. According to another embodiment, said aloe-vera leaf and allantoin are mixed together at a temperature less than 10° C. prior to step (iii). According to another embodiment, said temperature less than 10° C. is about 5° C. According to another embodiment, said temperature is about 5° C. According to another embodiment, said temperature is 5-100° C. According to another embodiment, said mixing is homogenizing.

If the topical pharmaceutical compositions of the present invention are formulated as an aerosol and applied to the skin as a spray-on, a propellant is added to a solution composition. A more complete disclosure of propellants useful herein can be found in Sagarin, Cosmetics Science and Technology, 2nd Edition, Vol. 2, pp. 443-465 (1972).

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additional objects, advantages, and novel features of the present invention will become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

EXAMPLES

Example 1—Preparation of Mineral-Based Compositions

The present example relates to a specific embodiment of the composition of the invention. Fountain water containing Sodium, Chloride, Calcium, Magnesium, Potassium, Manganese, Cooper, Zinc, Selenium, Sulphur, Silicates, Bicarbonate, Tellurium and Iron (pH 8.2) was collected and filtrated with reverse osmosis (RO) filtration system (6 Bar, 0.0001 micron; LOFMEM™ Q Series, Lenntech Ltd., Eaton Corporation, USA). Following drying and evaporation, the concentrate was grinded with citric acid to receive a supersaturated solution. Thereafter, a precipitation process (85° C.) is performed to substantial reduce sodium chloride levels. A dry substance is received by heating the supersaturated solution to 60° C.

Thereafter, a microencapsulating process is performed by mixing Jojoba wax with the supersaturated mineral substance (IKA® T18 digital ULTRA-TURRAX® Homogenizer, 25000 rpm) in 5° C., and subsequently mixing in vitamin E and vitamin A. Aloe-Vera dry leaf and allantoin are homogenized ((IKA® T18 digital ULTRA-TURRAX® Homogenizer, 25000 rpm, 5° C.) for 30 min following by an additional 30 min of homogenizing with the supersaturated mineral and vitamin mixture.

Example 2—Prevention of Skin Damage in Subjects Undergoing Radiotherapy

The ability of the composition described herein to prevent skin damage due to exposure to radiotherapy was examined. A breast cancer patient showed skin dermatitis including red irritation and blistering after 10 days of radiotherapy (FIG. 1A). Topically applying the composition of the invention remarkably cleared the dermatitis (FIG. 1B). Furthermore, dermatitis did not reoccur throughout the entire treatment process (26 seasons, 5 per week).

The present example shows prevention of damage to skin of a cancer patient undergoing radiotherapy by topically applying the composition of the invention.

Example 3—Prevention of Skin Damage in Subjects Exposed to UV Rays

The ability of the composition described herein to prevent skin damage (e.g., burns) due to over exposure to UV rays was examined. Fifty subjects, who were exposed to long term sun exposure, applied the composition in two different regimens. One group applied the composition each morning once a day and the second group applied the composition once every 3 days. Group one showed no signs of any burns or redness. The second group also showed no sign of burns. Two patients having very fair skin, showed minor redness after the 3rd day which disappeared after further application of the composition.

The present example shows prevention of damage to skin cells exposed to UV radiation by topical application of the composition of the invention.

Example 4—Prevention of Skin Cancer Reoccurrence

The ability of the composition described herein to delay the onset or return of skin cancers in subjects that had previous cancers removed and appeared to be prone to reoccurrence was examined. Three subjects applied the composition on a daily basis prior to exposure to the sun. No additional protection was used. All subjects were monitored every 3 months for a period of one year and then once every 6 months for a second year. None of the subjects had any reoccurrence of any skin cancers or precancerous growths during this treatment process.

The present example shows prevention of skin cancer reoccurrence by topical application of the composition of the invention.

Figure 2B:
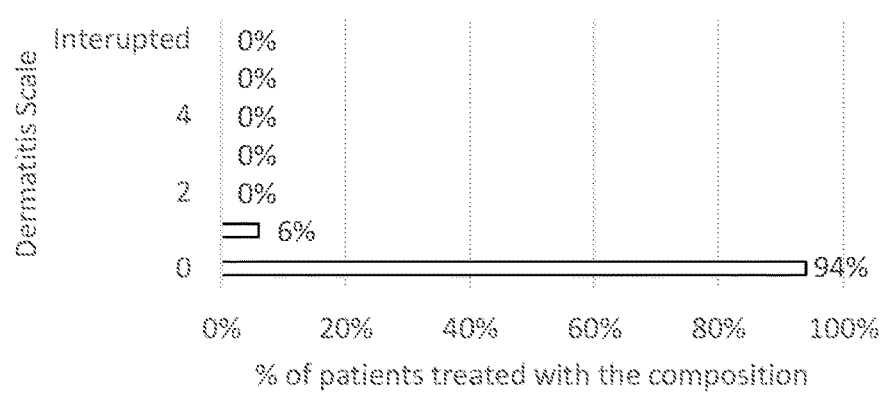
Figure 2C:
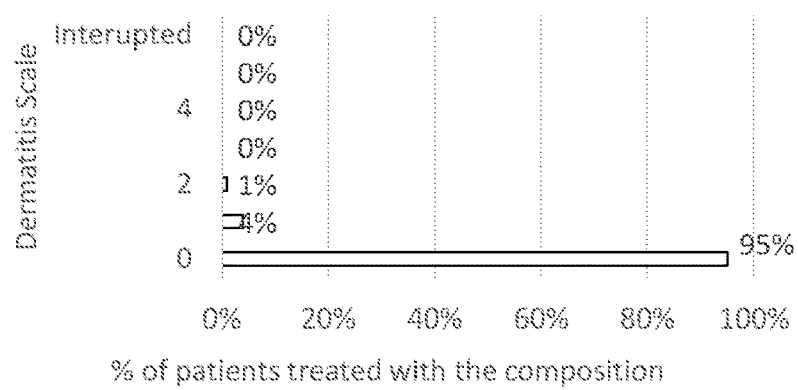
Figure 2D:
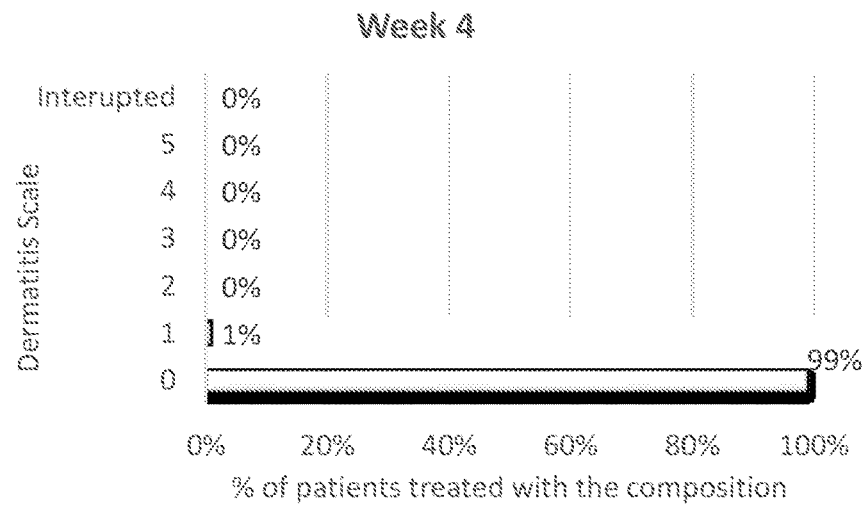
Figure 2E:
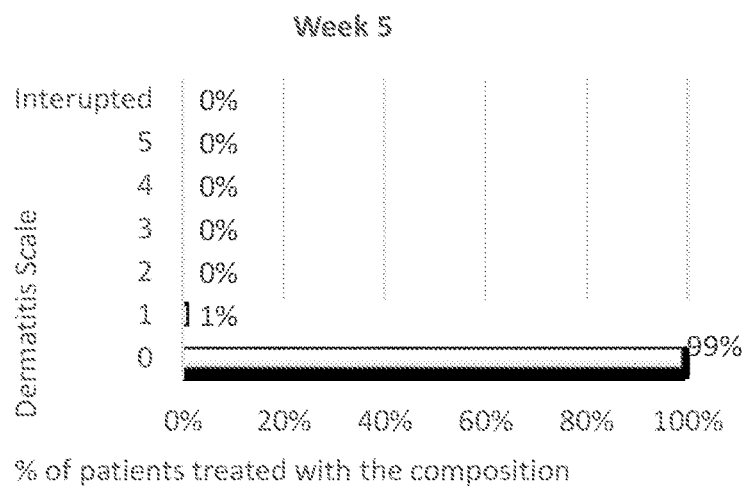
Figure 2F:
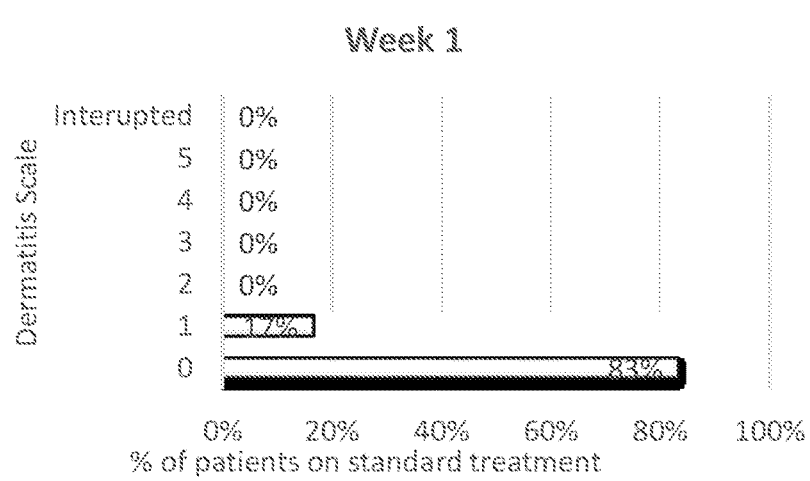
Figure 2G:
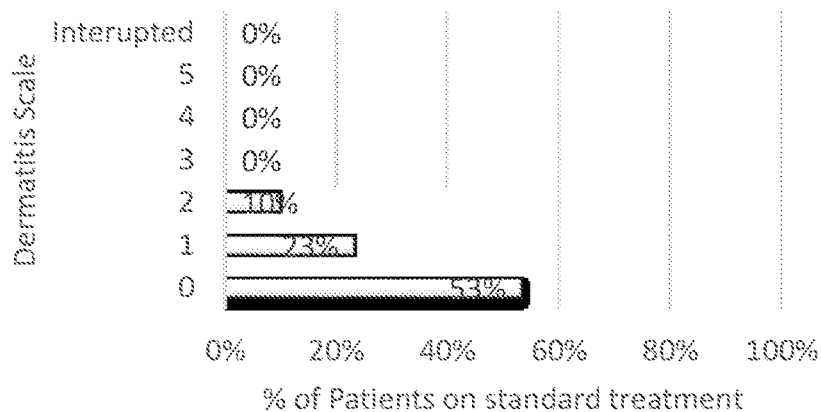
Figure 2H:
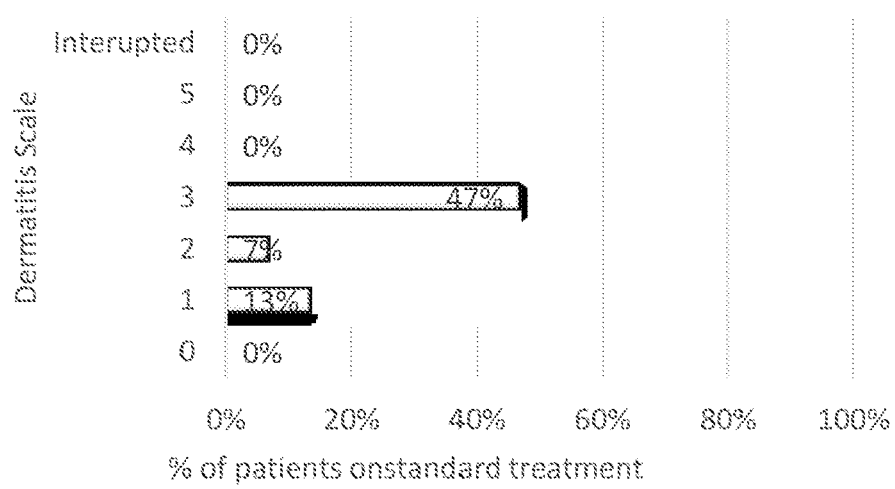
Figure 2I:
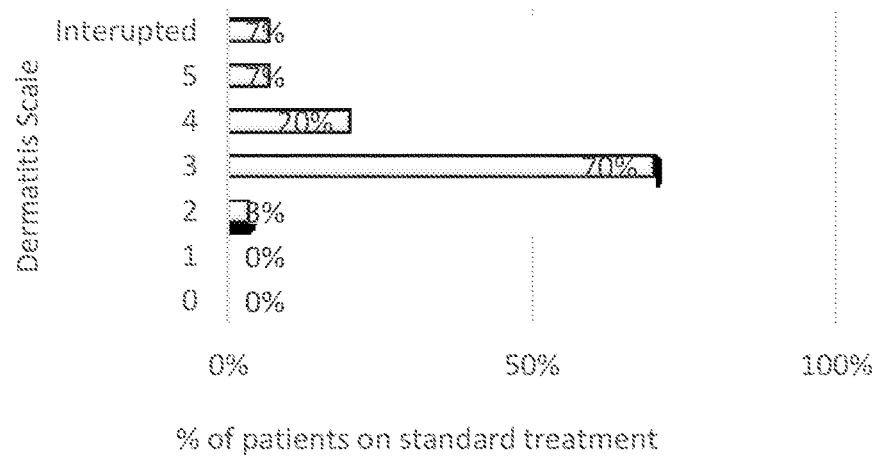
Figure 2J:
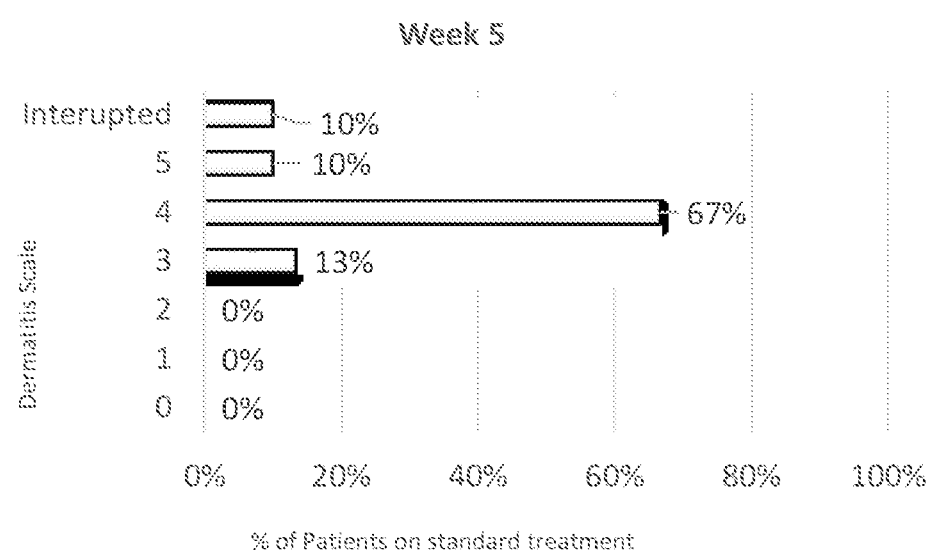

Example 5—Comparative Examination of the Composition and Petroleum and Oil Based Creams in Preventing Skin Damage in Subjects Exposed to Radiation The ability of the composition described herein to prevent skin damage (e.g., burns) due to radiation was examined compared to that of petroleum and oil based creams. Eighty breast cancer patients (lumpectomy and mastectomy) treated with radiation therapy participated in the study. Subjects received either the composition (containing allantoin) or a standard treatment (oil and petroleum cream). Fifty subjects (patients), applied the composition and thirty subjects (patients) applied other treatments identified as standard treatments. Skin toxicity, pain, itching, and skin-related quality of life scores were collected for up to 5 weeks during radiation treatment. Levels of radiation dermatitis in accordance with dermatological scale (see table 1) were assessed on a weekly basis for 5 weeks, results are presented as the percent of patients from each group exhibiting each level of radiation dermatitis (FIGS. 2A-J and table 2)

Results demonstrate that subjects who received the composition had a significantly lower average level of skin irritation than the Standard Treatment Group. Subjects treated with the composition suffered significantly reduced radiation induced dermatitis with no desquamation. And only mild erythema in early stages of treatment cycle. On the other hand, subjects treated with the standard treatments showed significant increased levels of dermatitis, desquamation and in some cases radiation treatment was stopped due to the severity of these effects.

TABLE 1

Toxicity grading of radiation dermatitis according to the National Cancer Institute-Common Terminology Criteria for Adverse Events

| Adverse event | Short name | Grade 1 | Grade 2 | Grade 3 | Grade 4 | Grade 5 |
|---|---|---|---|---|---|---|
| Rash: dermatitis associated with radiation | Dermatitis | Faint erythema or dry desquamation | Moderate to brisk erythema; patchy moist desquamation, mostly confined to skin folds and creases; moderate edema | Moist desquamation other than skin folds and creases; bleeding induced by minor trauma or abrasion | Skin necrosis or ulceration of full thickness dermis; spontaneous bleeding from involved site | Life Threatening |

TABLE 2

% of patients ranked in each of the composition to standard treatment in preventing skin damage in subjects exposed to radiation.

| | patients treated with the standard treatment (% of patients) week | | | | | patients treated with the composition (% of patients) week | | | | |
|---|---|---|---|---|---|---|---|---|---|---|
| Dermatitis Range | 1 | 2 | 3 | 4 | 5 | 1 | 2 | 3 | 4 | 5 |
| 0 | 83% | 67% | 0% | 0% | 0% | 100% | 94% | 46% | 48% | 24% |
| 1 | 17% | 23% | 40% | 0% | 0% | 0% | 6% | 50% | 52% | 76% |
| 2 | 0% | 10% | 33% | 27% | 13% | 0% | 0% | 4% | 0% | 0% |
| 3 | 0% | 0% | 27% | 63% | 73% | 0% | 0% | 0% | 0% | 0% |
| 4 | 0% | 0% | 0% | 7% | 7% | 0% | 0% | 0% | 0% | 0% |
| 5 | 0% | 0% | 0% | 0% | 0% | 0% | 0% | 0% | 0% | 0% |
| Interrupted | 0% | 0% | 0% | 3% | 7% | 0% | 0% | 0% | 0% | 0% |

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A process for preparing an emulsion stable topical formulation comprising a microencapsulation of one or more minerals and an emulsion, the process comprising:
   (i) providing a mineral-based compositions comprising selenium (Se) and zinc (Zn); wherein said selenium and said zinc have a concentration ratio of 1:1 to 10:1;
   (ii) mixing said mineral-based composition with a carrier at a temperature less than 10° C.; and
   (iii) mixing the composition of step (ii) with at least one additional ingredient selected from vitamin E, vitamin A, aloe-vera leaf and allantoin at a temperature of about 5° C.

2. The process of claim 1, wherein said aloe-vera leaf and allantoin are mixed together at a temperature less than 10° C. prior to step (iii).

3. The process of claim 1, wherein said mixing in step (ii) and step (iii) is homogenizing.

4. The process of claim 1, wherein said formulation has a pH level in the range of 5-7.

5. The process of claim 4, wherein said pH level is obtained by adding citric acid or a derivative thereof to the mineral-based composition of (i).

6. The process of claim 1, wherein said selenium (Se) has a concentration of 40-1000 mg/l.

7. The process of claim 1, wherein said zinc (Zn) has a concentration of 4-1000 mg/l.

8. The process of claim 1, wherein the carrier is selected from the group consisting of jojoba oil, coconut oil, aloe vera gel, cocoa butter, lecithin, almond oil, borage oil, canola oil, grape seed oil, olive oil, soybean oil, sunflower oil, wheat germ oil, apricot kernel oil, carrot oil, mango butter, evening primrose oil, black currant oil, avocado oil, macrocrystalline wax, paraffin, petrolatum, ozokerite, montan wax, beeswax, lanolin or a derivative, candelilla wax, ouricury wax, carnauba wax, Japan wax, cocoa butter, sugarcane wax, cork fiber wax, and mixtures thereof.

9. The process of claim 1, wherein the carrier is selected from jojoba oil, coconut oil, aloe vera gel, and mixtures thereof.

10. The process of claim 1, wherein said mineral-based composition comprises less than 1000 mg/l sodium (Na).

11. The process of claim 1, wherein said mineral-based composition comprises less than 500 mg/l chloride.

12. The process of claim 1, wherein said mineral-based composition comprises 50-500 mg/l of sodium, 25000-40000 mg/l potassium, 5000-120000 mg/l calcium, 20000-30000 mg/l magnesium, 50-150 mg/l chloride, 2000-2500 mg/l sulfate, 85-100 mg/l bromide, 5-70 mg/l manganese, 10-50 mg/l copper, 3-80 mg/l sulfur, 5-50 mg/l silica, 10-800 mg/l bicarbonate, and 0.05-0.5 mg/l tellurium.

* * * * *